US008841447B2

(12) United States Patent
Marom et al.

(10) Patent No.: US 8,841,447 B2
(45) Date of Patent: Sep. 23, 2014

(54) PROCESS FOR THE PREPARATION OF ALOGLIPTIN

(75) Inventors: Ehud Marom, Kfar Saba (IL); Michael Mizhiritskii, Rehovot (IL); Shai Rubnov, Tel Aviv (IL)

(73) Assignee: Mapi Pharma Ltd., Ness Ziona (IL)

( * ) Notice: Subject to any disclaimer, the term of this patent is extended or adjusted under 35 U.S.C. 154(b) by 275 days.

(21) Appl. No.: 13/258,816

(22) PCT Filed: Mar. 25, 2010

(86) PCT No.: PCT/IL2010/000260
§ 371 (c)(1),
(2), (4) Date: Sep. 22, 2011

(87) PCT Pub. No.: WO2010/109468
PCT Pub. Date: Sep. 30, 2010

(65) Prior Publication Data
US 2012/0029000 A1 Feb. 2, 2012

Related U.S. Application Data

(60) Provisional application No. 61/163,481, filed on Mar. 26, 2009.

(51) Int. Cl.
| | |
|---|---|
| *C07D 401/04* | (2006.01) |
| *A61K 31/506* | (2006.01) |
| *A61P 19/02* | (2006.01) |
| *C07D 239/62* | (2006.01) |
| *C07C 275/24* | (2006.01) |
| *C07D 403/04* | (2006.01) |
| *A61K 31/513* | (2006.01) |
| *C07D 239/545* | (2006.01) |
| *C07C 275/50* | (2006.01) |

(52) U.S. Cl.
CPC ............ *A61K 31/513* (2013.01); *C07D 239/62* (2013.01); *C07C 275/24* (2013.01); *C07D 403/04* (2013.01); *C07D 239/545* (2013.01); *C07C 275/50* (2013.01)
USPC ......................................... 544/309; 514/274

(58) Field of Classification Search
USPC .......................................... 544/309; 514/274
See application file for complete search history.

(56) References Cited

U.S. PATENT DOCUMENTS

| | | | |
|---|---|---|---|
| 2,598,936 A | 6/1952 | Papesch et al. | |
| 4,089,959 A | 5/1978 | Diamond | |
| 5,719,279 A | 2/1998 | Kuefner-Muehl et al. | |
| 6,066,641 A | 5/2000 | Cavalla et al. | |
| 6,248,746 B1 | 6/2001 | Chasin et al. | |
| 7,378,423 B2* | 5/2008 | Kawasaki et al. | 514/264.1 |
| 7,781,584 B2* | 8/2010 | Feng et al. | 544/309 |
| 7,795,428 B2* | 9/2010 | Feng et al. | 544/309 |
| 8,188,275 B2* | 5/2012 | Feng et al. | 544/309 |
| 8,222,411 B2* | 7/2012 | Feng et al. | 544/314 |
| 2004/0097510 A1 | 5/2004 | Himmelsbach et al. | |
| 2007/0066635 A1 | 3/2007 | Andres et al. | |
| 2007/0066636 A1 | 3/2007 | Chyall et al. | |
| 2008/0194593 A1 | 8/2008 | Kalla et al. | |
| 2008/0312228 A1 | 12/2008 | Kawasaki et al. | |

FOREIGN PATENT DOCUMENTS

| | | |
|---|---|---|
| EP | 1083172 A1 | 3/2001 |
| EP | 1586571 A1 | 10/2005 |
| WO | 94/03456 A1 | 2/1994 |
| WO | 01/29010 A1 | 4/2001 |
| WO | 2005/095381 A1 | 10/2005 |
| WO | 2005/121142 A1 | 12/2005 |
| WO | 2007/035372 A2 | 3/2007 |
| WO | 2007/035379 A1 | 3/2007 |
| WO | 2007/035629 A2 | 3/2007 |
| WO | 2007/150011 A2 | 12/2007 |
| WO | 2008/067465 A1 | 6/2008 |
| WO | 2009/011451 A1 | 1/2009 |
| WO | 2010/089686 A1 | 8/2010 |

OTHER PUBLICATIONS

Aimoto, Saburo (2001) Contemporary Methods for Peptide and Protein Synthesis. Current Organic Chemistry 5(1):45-87.
Armstrong, Joseph D. III et al., (1997) A novel synthesis of disubstituted ureas using titanium(IV) isopropoxide and sodium borohydride. Tetrahedron Lett 38(9):1531-1532.
Artuso, Emma et al., (2007) Preparation of Mono-, Di-, and Trisubstituted Ureas by Carbonylation of Aliphatic Amines with S,S-Dimethyl Dithiocarbonate. Synthesis 2007(22):3497-3506.
Feng, Jun et al., (2007) Discovery of alogliptin: a potent, selective, bioavailable, and efficacious inhibitor of dipeptidyl peptidase IV. J Med Chem 50(10):2297-2300 Erratum: J Med Chem (2008) 51(14):4357-4358.
Gabriele, Bartolo et al., (2004) Efficient Synthesis of Ureas by Direct Palladium-Catalyzed Oxidative Carbonylation of Amines. J Org Chem 69(14):4741-4750.
Hancock, Bruno C. et al., (2002) Polyamorphism: a pharmaceutical science perspective. J Pharm Pharmacol 54 (8):1151-1152.
Montalbetti, Christian A. G. N. and Falque, Virginie (2005) Amide bond formation and peptide coupling. Tetrahedron 61(46):10827-10852.
Nagamatsu, Tomohisa et al., (1994) Isolation of new chlorinated regioisomers of mono N-substituted uracil derivatives and synthesis of 3-substituted 8-phenylpyrimido[5,4-e]-1,2,4-triazine-5,7 (6H,8H)-diones. Heterocycles 37 (2)1147-1164.
Papesch, Victor and Schroeder, Elmer F. (1951) Synthesis of 1-Mono- and 1,3-Di-Substituted 6-Aminouracils. Diuretic Activity. J Org Chem 16(2):1879-1890.

(Continued)

*Primary Examiner* — Venkataraman Balasubramanian
(74) *Attorney, Agent, or Firm* — Rothwell, Figg, Ernst & Manbeck, P.C.

(57) ABSTRACT

The present invention is based on the discovery of a process for preparing pyrimidin-dione compounds, especially alogliptin and its derivatives, which comprises the reaction of a urea derivative of formula (VIII) with a malonic acid or its derivatives to form intermediates of formulae (VII) or (VII-A), which are subsequently converted to a compound of formula (II) upon introduction of a leaving group X. Compound (II) then reacts with an amine to form compound (I), which is optionally converted to its salts of formula (IV).

18 Claims, No Drawings

(56) References Cited

OTHER PUBLICATIONS

Sun, Hongmao et al., (1999) Molecular modeling and synthesis of inhibitors of herpes simplex virus type 1 uracil-DNA glycosylase. J Med Chem 42(13):2344-2350.

Tafesh, Ahmed M and Weigunty, Jens (1996) A Review of the Selective Catalytic Reduction of Aromatic Nitro Compounds into Aromatic Amines, Isocyanates, Carbamates, and Ureas Using CO. Chem Rev 96(6):2035-2052.

Zhou, W. -J. and Kurth, M. J. (2001) Synthesis of a novel pH-responding polymer with pendant barbituric acid moieties. Polymer 42(1):345-349.

International Search Report of PCT/IL10/00260 mailed Jul. 1, 2010, 2 pages.

International Search Report and Written Opinion of PCT/IL10/00378 mailed Nov. 5, 2010, 9 pages.

International Search Report of PCT/IL10/00974 mailed Mar. 23, 2011, 2 pages.

Supplementary Search Report from European Patent Appln. No. 10755533 dated Sep. 5, 2012, 7 pages.

Database CA [Online] Chemical Abstracts Service, Columbus, Ohio, US; Adzhibekyan, A. S. et al: "Some 5- and N-arylsubstituted barbiturates and their biological properties", XP002682831, retrieved from STN Database accession No. 1976:30997 & Adzhibekyan, A. S. et al: "Some 5- and N-arylsubstituted barbiturates and their biological properties", Armyanskii Khimicheskii Zhurnal , 28(9), 741-6 Coden: Aykzan; ISSN: 0515-9628, 1975, 2 pages.

Database CA [Online] Chemical Abstracts Service, Columbus, Ohio, US; Krasnov, K. A. et al: "Specificity of methylation by dimethyl sulfate of barbituric acid salts and alkyl derivatives", XP002682832, retrieved from STN Database accession No. 1998:122290, 3 pages.

Database CA [Online] Chemical Abstracts Service, Columbus, Ohio, US; Khazhakyan, L. V. et al: "IR study of tautomeric equilibrium and intermolecular interaction of some barbituric and thiobarbituric acid derivatives", XP002682833, retrieved from STN Database accession No. 1977:188599, 1 page.

Database CA [Online] Chemical Abstracts Service, Columbus, Ohio, US; Kaldrikyan, M. A. et al: "Pyrimidine derivatives. XIX. N-Substituted thiobarbituric and barbituric acids", XP002682834, retrieved from STN Database accession No. 1972:419603, 2 pages.

Database CA [Online] Chemical Abstracts Service, Columbus, Ohio, US; Lyons, Edward et al: "Identification of alkylbarbituric acids", XP002682835, retrieved from STN Database accession No. 1929:7035, 1 page.

Database Registry [Online] Chemical Abstracts Service, Columbus, Ohio, US; Jan. 16, 2004, XP002682836, retrieved from STN Database accession No. 638137-64-1, 1 page.

Database Registry [Online] Chemical Abstracts Service, Columbus, Ohio, US; Mar. 20, 2003, XP002682837, retrieved from STN Database accession No. 500114-36-3, 1 page.

Database Registry [Online] Chemical Abstracts Service, Columbus, Ohio, US; Sep. 30, 2007, XP002682838, retrieved from STN Database accession No. 948822-94-4, 2 pages.

Database Registry [Online] Chemical Abstracts Service, Columbus, Ohio, US; Feb. 12, 2009, XP002682839, retrieved from STN Database accession No. 1104731-42-1, 1 page.

Database CA [Online] Chemical Abstracts Service, Columbus, Ohio, US; Cowden, William B.: "Unexpected transaminations of some aminopyrimidin-4(3H)-ones", XP002682841, retrieved from STN Database accession No. 1986:553018, 1 page.

Rodriguez-Spong et al., (2004) General principles of pharmaceutical solid polymorphism: a supramolecular perspective. Adv Drug Deliv Rev 56: 241-274.

Lee et al., (2008) Pharmacokinetic, pharmacodynamic, and efficacy profiles of alogliptin, a novel inhibitor of dipeptidyl peptidase-4, in rats, dogs, and monkeys. Eur J Pharmacol 589: 306-14.

Xu et al., (2009) Alogliptin, a novel antidiabetic agent. Chinese Journal of New Drugs and Clinical Remedies 28(1): 66-69. Abstract only.

\* cited by examiner

PROCESS FOR THE PREPARATION OF ALOGLIPTIN

CROSS REFERENCE TO RELATED APPLICATIONS

This application is a 35 U.S.C. §371 National Phase Entry Application from PCT/IL2010/000260, filed Mar. 25, 2010, and designating the United States, which claims the benefit of U.S. Provisional Application No. 61/163,481, filed on Mar. 26, 2009, which are incorporated herein in their entireties.

FIELD OF THE INVENTION

The present invention relates to a process for the preparation of alogliptin and its analogs, inhibitors of dipeptidyl peptidase-4 (DPP-4) that are useful for the treatment of type 2 diabetes.

BACKGROUND OF THE INVENTION

Diabetes affects millions of people worldwide and is considered one of the main threats to human health in the 21$^{st}$ century. In 2006, the World Health Organization (WHO) estimated that over 180 million people worldwide had diabetes, and the number is projected to double by 2030. Over time, uncontrolled diabetes can damage body systems, including the heart, blood vessels, eyes, kidneys and nerves. According to the WHO, approximately 1.1 million people died from diabetes in 2005, and it is estimated that diabetes-related deaths will increase by more than 50% in the next decade. Globally, the socioeconomic burden of diabetes is substantial.

There are two main types of diabetes, designated type 1 and type 2, with type 2 diabetes accounting for over 90% of all diabetes cases globally. Type 1 diabetes is characterized by insulin deficiency, primarily caused by autoimmune-mediated destruction of pancreatic islet β-cells, and type 2 diabetes is characterized by abnormal insulin secretion and concomitant insulin resistance. To prevent the development of ketoacidosis, people with type 1 diabetes must take exogenous insulin for survival. Although those with type 2 diabetes are not dependent on exogenous insulin as much as subjects with type 1 diabetes, they may require exogenous insulin to control blood glucose levels.

As diabetes has become a global health concern, research interest in the condition has rapidly increased. In addition to studies on prevention, many studies with the aim of developing new interventions for the treatment of diabetes, especially type 2 diabetes, have been conducted. Currently available medications for the treatment and management of type 2 diabetes include metformin, sulfonylureas, thiazolidinediones and insulin. However, these therapies are commonly associated with secondary failure and may cause hypoglycemia. Insulin resistance and progressively worsening hyperglycemia caused by reduced β-cell function are major challenges in managing type 2 diabetes. Evidence suggests that patients with insulin resistance do not develop hyperglycemia until their β-cells are unable to produce enough insulin. New agents that can enhance insulin secretion from islet β-cells in a sustained glucose-dependent manner could therefore hold promise for the treatment of type 2 diabetes.

One promising approach is based on inhibition of the serine protease dipeptidyl-peptidase IV (DPP IV), a postproline dipeptidyl aminopeptidase that belongs to the S9b peptidase family of proteolytic enzymes. It is known that DPP IV plays a key role in maintaining glucose homeostasis by controlling the incretin activity of glucagon-like peptide 1 (GLP-1) and glucose-dependent insulinotropic polypeptide (GIP, also known as gastric inhibitory polypeptide). Inhibition of DPP IV is therefore recognized as a novel therapeutic approach for the treatment of type 2 diabetes.

Recently, a series of DPP IV inhibitors were developed. Among these highly potent compounds, alogliptin benzoate (SYR-322) and its analogs demonstrated encouraging antidiabetic efficacy (EP 1586571 (WO 2005/095381); WO 2008/067465; WO 2007/035379, and US 2004/097510).

Alogliptin benzoate can be prepared as described in EP 1586571 (WO 2005/095381) according to the process set forth in Scheme 1:

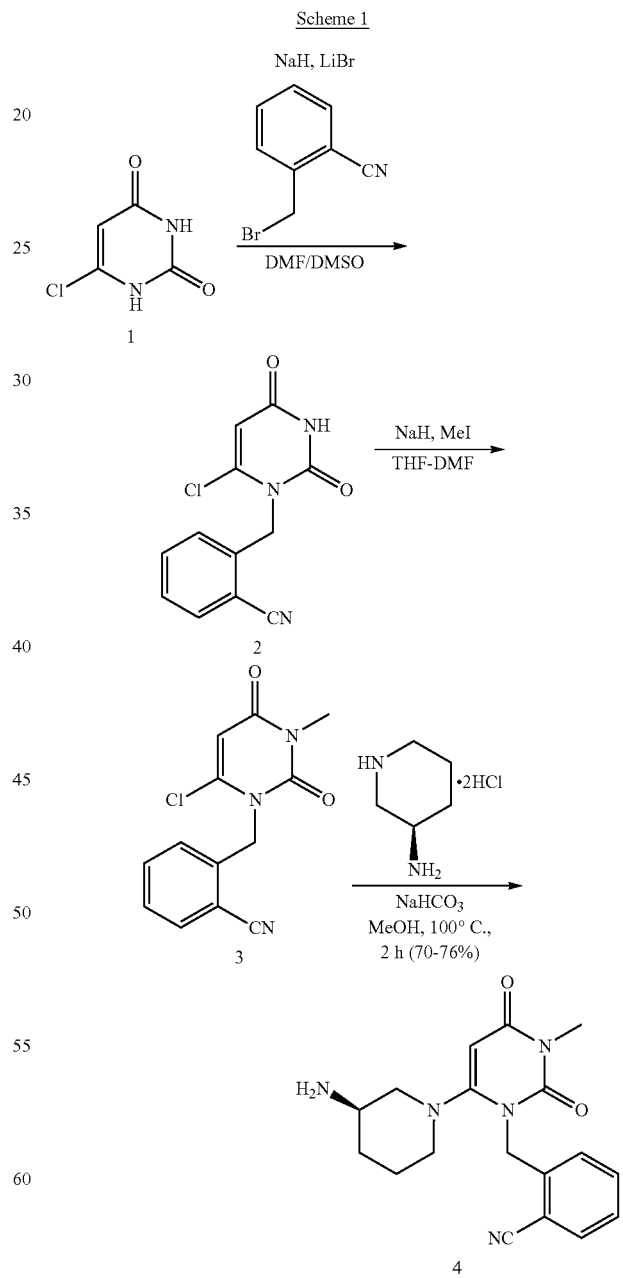

In accordance with this process, 6-Chlorouracil (1) is alkylated with 2-(bromomethyl)benzonitrile in the presence of NaH and LiBr in a mixture of DMF-DMSO to produce the N-benzyluracil derivative (2) in 54% yield. Compound (2) is further alkylated with iodomethane and NaH in DMF/THF to give the 1,3 disubstituted uracil (3) in 72% yield. Subsequent displacement of chlorouracil (IV) with 3(R)-aminopiperidine dihydrochloride in the presence of either NaHCO$_3$ in hot methanol or K$_2$CO$_3$ in aqueous isopropanol provides alogliptin (4), which is isolated as the corresponding benzoate salt by treatment with benzoic acid in ethanol. The overall yield of this three-stage process is ~20-25%. One of the disadvantages of above described process is the difficulty to separate and purify mixtures of solvents with high boiling point (for example, DMF/DMSO) for recycling. Another disadvantage is the usage of hazardous materials such as sodium hydride, which requires anhydrous solvents as a reaction media.

Intermediate 2-((6-chloro-3-methyl-2,4-dioxo-3,4-dihydropyrimidin-1(2H)-yl)methyl)benzonitrile (3) is alternatively obtained by alkylation of 6-chloro-3 methyluracil with 2-(bromomethyl)benzonitrile by means of diisopropylethylamine in hot NMP (WO 2007/035629). Although this process is more technological than the previously described process (EP 1586571), the overall yield is still moderate (50-55%). The problem of mixed solvents (toluene, NMP, diisopropylethylamine) separation persists for this process as well.

Consequently, there is a long-felt need for a process for the preparation of alogliptin and related derivatives which not only overcomes the problems in the art processes as mentioned above, but is also safe, cost effective, and industrially feasible.

SUMMARY OF THE INVENTION

The present invention is based on the discovery of a process for preparing pyrimidin-dione compounds, especially alogliptin and its salts and derivatives, which comprises the reaction of a urea derivative of formula (VIII) with a malonic acid or its derivatives to form intermediates of formulae (VII) or (VII-A), which are subsequently converted to a compound of formula (II) upon introduction of a leaving group X. Compound (II) then reacts with an amine to form compound (I), which is optionally converted to its salts of formula (IV). One or more steps in this process can be conducted in one stage, without isolation or purification of intermediates. The process of the invention is safe, cost-effective and can be conducted on industrial scale without facing the problems of prior art procedures.

Thus, in one embodiment, the present invention provides a process for producing a pyrimidin-dione derivative represented by the structure of formula (I):

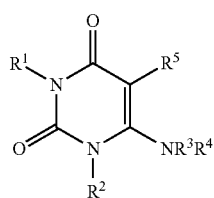

(I)

wherein:
R$^1$ and R$^5$ are each independently H or (C$_1$-C$_{10}$)alkyl,
R$^2$ is CH$_2$Ar; and
R$^3$ and R$^4$ together with the nitrogen to which they are attached form a 4, 5, 6 or 7 membered ring, which may be unsubstituted or substituted;

the process comprising the following steps:
1) reacting a urea derivative of formula (VIII):

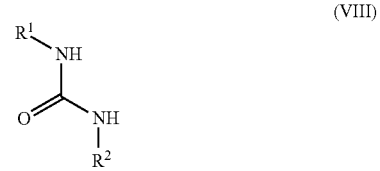

(VIII)

with malonic acid or its derivatives of formulae RO$_2$CCH(R$^5$)CO$_2$R or RO$_2$CCH(R$^5$)CN, under conditions sufficient to form a compound of formula (VII) or (VII-A):

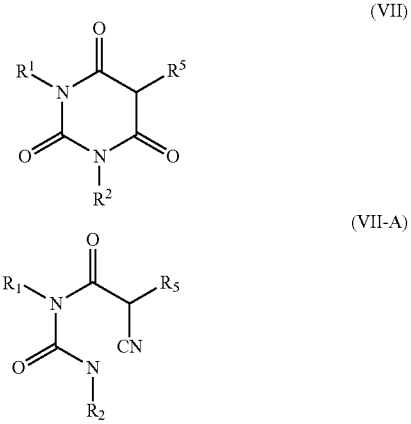

(VII)

(VII-A)

wherein R$^1$, R$^2$ and R$^5$ are as defined above, and R is H, (C$_1$-C$_{10}$)alkyl, phenyl or N-oxysuccinimidyl, wherein each of the alkyl and phenyl can be substituted or unsubstituted;

2) reacting compounds (VII) or (VII-A) with a reagent that introduces or forms the group X, under conditions sufficient to form a compound of the formula (II):

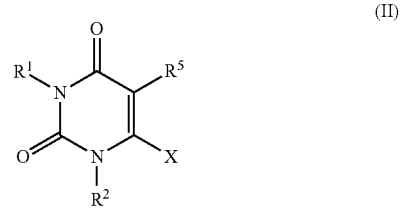

(II)

wherein X is a leaving group; and
3) reacting compound (II) with a reagent of Formula (III): HNR$^3$R$^4$ under conditions sufficient to form the compound of Formula (I):

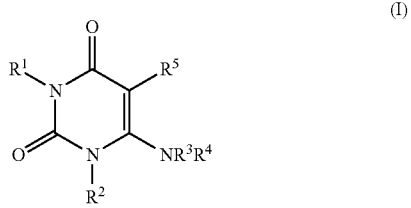

(I)

In one particular embodiment, step (1) comprises a reaction between urea (VIII) and a malonic acid ester of formula RO₂CCH(R⁵)CO₂R, so as to generate a compound of formula (VII). In another particular embodiment, step (1) comprises a reaction between urea (VIII) and a derivative of formula RO₂CCH(R⁵)CN, so as to generate a compound of formula (VII-A). Each possibility represents a separate embodiment of the invention.

Optionally, the process further comprises the step of converting the pyrimidin-dione product of formula (I) to a salt of formula (IV)

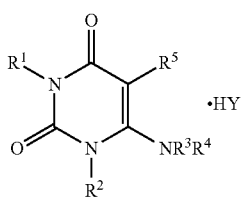

(IV)

wherein Y is a counter-ion selected from the group consisting of acetate, trifluoroacetate, citrate, hydrochloride, L-lactate, succinate, benzoate and L-tartrate. In accordance with this step, compound (I) is reacted with an acid HY to generate the corresponding salt. A currently preferred salt is the benzoate salt. Examples of the acid HY include, but are not limited to, acetic acid (Y=acetate), trifluoroacetic acid (Y=trifluoroacetate), citric acid (Y=citrate), hydrochloric acid (Y=Cl), L-lactic acid (Y=L-lactate), succinic acid (Y=succinate), benzoic acid (Y=benzoate), and L-tartaric acid (Y=L-tartrate). Each possibility represents a separate embodiment of the invention.

In one embodiment, the steps of reacting compound (II) with an amine of formula (III) to generate compound (I) followed by a reaction with an acid HY are conducted in one stage without separation or purification of any intermediates.

The group X can be any leaving group, but is generally selected from a halogen (Hal=F, Cl, Br or I), a sulfonate (e.g., tosylate (OTs), mesylate (OMs) and the like), a sulfide (e.g., SMe, SPh and the like), imidazole (Im), benzotriazole (Bta), NH₂ and the like. Each possibility represents a separate embodiment of the invention.

In one currently preferred embodiment, X is Hal and step (2) comprises reacting a compound of formula (VII)

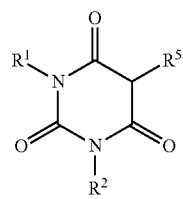

(VII)

with a halogen containing reagent, under conditions sufficient to introduce the group X. Exemplary halogen-containing reagents include, but are not limited to, phosphorous oxychloride, phosphorous pentachloride, thionyl chloride, phosphorous tribromide and N-bromosuccinimide, as well as any other halogen-containing reagents known to a person of skill in the art. Each possibility represents a separate embodiment of the invention.

The malonic acid derivative of formula (VII) or (VII-A) can be malonic acid or is a malonic acid ester such as methyl, ethyl, phenyl or N-oxysuccinimidyl ester, or the corresponding nitrile derivative.

The amine HNR³R⁴ is a cyclic moiety in which R³ and R⁴ together with the nitrogen to which they are attached form a 4, 5, 6 or 7 membered ring, which may be substituted. In one embodiment, HNR³R⁴ is a diamine of formula (V): HNR⁶R⁷—NHR⁸, wherein R⁶ and R⁷ together with the nitrogen to which they are attached form a 4, 5, 6 or 7 membered ring, NHR⁸ is a substituent of such ring, and R⁸ is H or a nitrogen protecting group. In one currently preferred embodiment, HNR³R⁴ is represented by the structure:

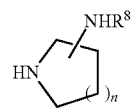

wherein R⁸ is H or a nitrogen protecting group, and n is 0, 1 or 2 (thus defining a 5, 6 or 7 membered ring). The substituents NHR⁸ can be located at any position on the ring. In another currently preferred embodiment, HNR³R⁴ is represented by the structure

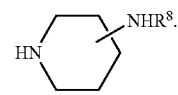

Each possibility represents a separate embodiment of the invention.

The protecting group R⁸ can be any nitrogen protecting group known to a person of skill in the art. Such protecting groups include acid labile protecting groups, base labile protecting groups, or protecting groups that are removable under neutral conditions. In accordance with one currently preferred embodiment, R⁸ is an acid labile nitrogen protecting group such as tert-Butyloxycarbonyl (Boc).

In accordance with the embodiment wherein HNR³R⁴ is a diamine of formula (V): HNR⁶R⁷—NHR⁸, step (3) of the process of the invention comprises reacting a compound of formula (II) with diamine of (V) under conditions sufficient to form a compound of formula (VI):

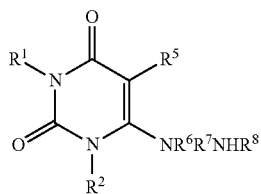

(VI)

wherein R¹, R² and R⁵, R⁶, R⁷ and R⁸ are as defined above.

In one currently preferred embodiment, the compound of formula (VI) is represented by the structure of formula (VI-A):

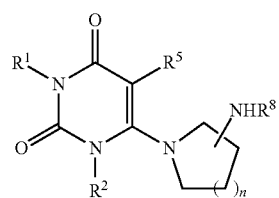

(VI-A)

wherein $R^1$, $R^2$, $R^5$, $R^8$ and n are as defined above.

In another currently preferred embodiment, the compound of formula (VI) is represented by the structure of formula (VI-B):

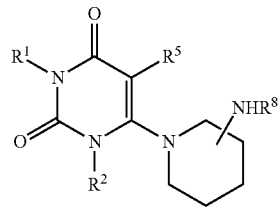

(VI-B)

wherein $R^1$, $R^2$, $R^5$, $R^8$ and n are as defined above.

In one embodiment, the steps of reacting compound (II) with a diamine of formula (V) to generate compound (VI) followed by reaction with an acid HY are conducted in one stage without separation or purification of any intermediates. In accordance with this embodiment, the process of the invention comprises the steps of: (a) reacting a compound of formula (II) with a diamine of formula (V) under conditions sufficient to form compound (VI); (b) reacting compound (VI) with acid HY to form a salt as one-stage synthesis without separation and purification of compound (VI); and (c) optionally, if needed, removing the protecting group so as to form a compound of formula (I). Y is a counter-ion selected from the group consisting of acetate, trifluoroacetate, citrate, hydrochloride, L-lactate, succinate, benzoate and L-tartrate.

In one currently preferred embodiment of the present invention, $R^1$ is a ($C_1$-$C_{10}$) alkyl, preferably methyl. In another currently preferred embodiment, $R^2$ is —($CH_2$)-(2-cyanophenyl). In accordance with another preferred embodiment of the present invention, $R^5$ is H. In accordance with yet another currently preferred embodiment, $R^3$ and $R^4$ together with the nitrogen to which they are attached form a ring represented by the structure:

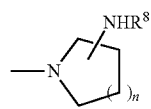

wherein $R^8$ is H or a nitrogen protecting group (preferably Boc), and n is 0, 1 or 2. In one embodiment, $R^3$ and $R^4$ together with the nitrogen to which they are attached form a ring represented by the structure:

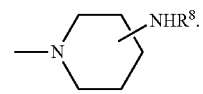

In another embodiment, $R^3$ and $R^4$ together with the nitrogen to which they are attached form a ring represented by the structure:

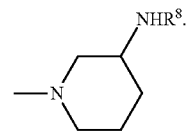

In another embodiment, $R^3$ and $R^4$ together with the nitrogen to which they are attached form a ring represented by the structure:

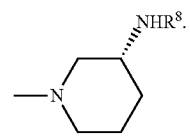

Each possibility represents a separate embodiment of the invention.

Preferably, the pyrimidin-dione of the formula (I) is 2-[6-[3(R)-Aminopiperidin-1-yl]-3-methyl-2,4-dioxo-1,2,3,4-tetrahydropyrimidin-1-ylmethyl]benzonitrile (alogliptin), or a salt thereof, especially the benzoate salt (alogliptin benzoate).

The present invention further relates to certain intermediates formed in the process described herein. Such intermediates are novel and form further aspects of the present invention.

Thus, in one embodiment, the present invention relates to a compound of the formula (VII), wherein the compound is represented by the structure:

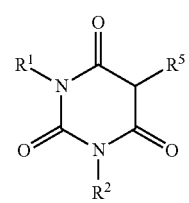

(VII)

wherein
$R^1$ is H or ($C_1$-$C_{10}$)alkyl,
$R^2$=$CH_2$Ar, and
$R^5$=H.

In a currently preferred embodiment, the compound of formula (VII) is represented by the structure:

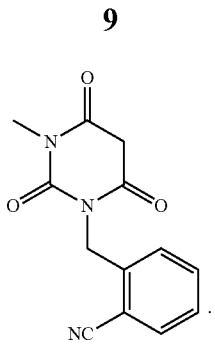

In another embodiment, the present invention relates to a compound of the formula (VII-A), wherein the compound is represented by the structure:

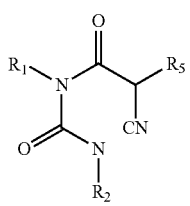

(VII-A)

wherein
$R^1$ is H or $(C_1-C_{10})$alkyl,
$R^2$=CH$_2$Ar, and
$R^5$=H.

In a currently preferred embodiment, the compound of formula (VII-A) is represented by the structure:

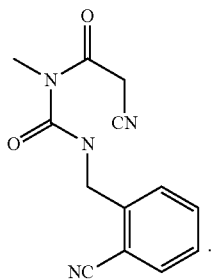

In another embodiment, the present invention relates to a compound of formula (VIII), wherein the compound is represented by the structure:

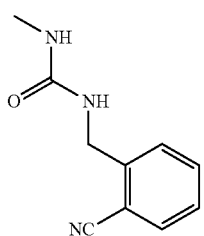

(VIII)

In yet another embodiment, the present invention relates to a compound of formula (VI), wherein the compound is represented by the structure:

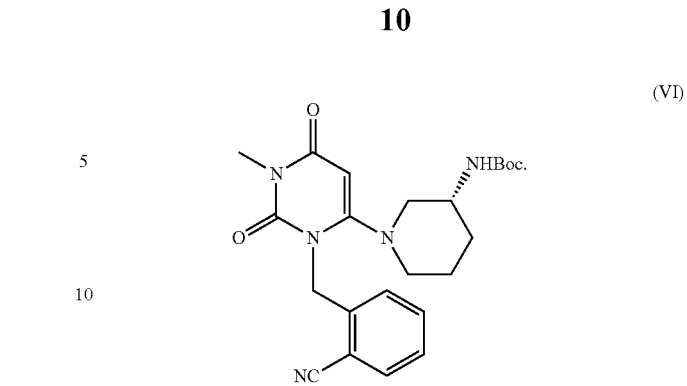

(VI)

In another embodiment, the present invention relates to a compound of formula (I), or a salt of formula (IV), wherein such compounds are prepared in accordance with the processes described herein.

In another embodiment, the present invention relates to a compound of formula (I), or a salt of formula (IV), wherein such compounds are prepared in accordance with the processes described herein, for use in the treatment of diabetes, preferably type-2 diabetes.

In another embodiment, the present invention relates to a method of treating diabetes, preferably type-2 diabetes, comprising the step of administering to a subject in need thereof a compound of formula (I), or a salt of formula (IV), wherein such compounds are prepared in accordance with the processes described herein.

In another embodiment, the present invention relates to the use of a compound of formula (I), or a salt of formula (IV), wherein such compounds are prepared in accordance with the processes described herein for the preparation of a medicament to treat diabetes, preferably type-2 diabetes.

DETAILED DESCRIPTION OF THE INVENTION

The applicants have now found a process (Scheme 2), by which the compound of formula (IV) (e.g., alogliptin salts such as alogliptin benzoate) may be prepared on a manufacturing scale from the compound of formula (VIII):

Scheme 2

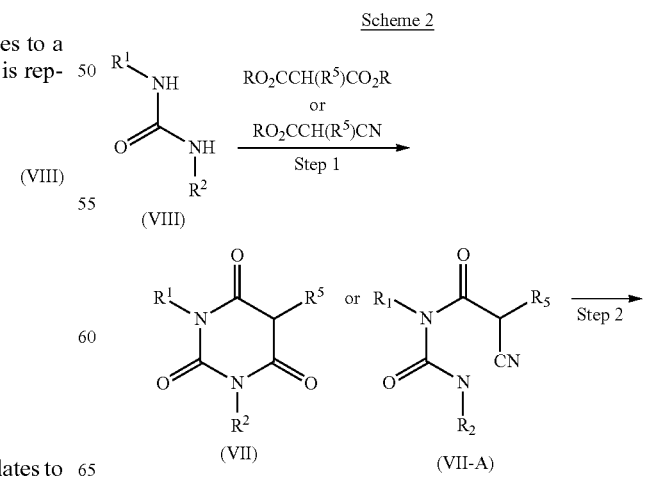

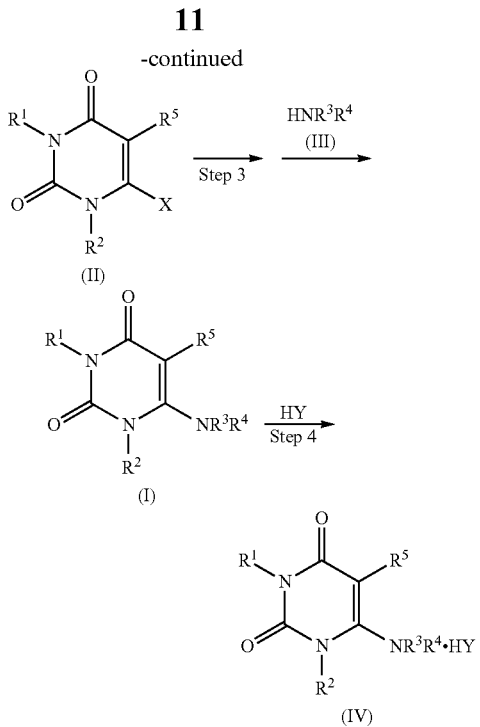

Step 1

Compound (VII) can be obtained by reacting compound (VIII) with malonic acid or the ester of formula $RO_2CCH(R^5)CO_2R$. Compound (VII-A) can be obtained by reacting compound (VIII) with the corresponding nitrile derivative of formula $RO_2CCH(R^5)CN$ (e.g., cyanoacetic acid or its ester). These reactions are preferably conducted in a solvent and at a temperature ranging from room temperature to reflux. Preferably, the process comprises the following steps:

(1) allowing the malonic acid or the malonate ester or the nitrile derivative (e.g., cyanoacetic acid or its esters) to react with the substituted urea (VIII), for example at a molar ratio of about 1.0-1.3:1.0-1.2 in a solvent in the presence or absence of a catalyst in a reactor at a temperature of about 60-120° C. under stirring and refluxing for a time period of about 5-10 h, followed by cooling; and (2) pouring over ice water, filtering, washing the filtered solid with water, and with an organic solvent, e.g., methyl-tert-butylether, and recrystalyzing to obtain compound (VII) or (VII-A).

In one embodiment, the malonate derivative is a malonic acid derivative (i.e., $RO_2CCH(R^5)CO_2R$ wherein R is H). In another embodiment, the malonate derivative is a malonate ester (i.e., $RO_2CCH(R^5)CO_2R$), such as methyl, ethyl, phenyl esters and the like, as well as active esters, such as succinimidyl, nitrophenyl, pentafluorophenyl and the like. In one particular embodiment, the malonate ester is dimethyl malonate. In another particular embodiment, the malonate ester is diethyl malonate. In another embodiment, the malonate derivative is a nitrile derivative (i.e., $RO_2CCH(R^5)CN$) wherein R is as defined above, for example cyanoacetic acid or its ester. Each possibility represents a separate embodiment of the invention.

The reaction can further optionally employ a catalyst such as metal alkoxides or other organic bases, which accelerate this reaction. The catalyst, if used, can be, e.g., potassium tert-butoxide, sodium methoxide, sodium ethoxide, sodium isopropoxide and/or sodium n-butoxide. The amount of the catalyst can vary, but it is typically used in an amount of about 25-30% by weight based on the total weight of the malonate and urea derivative (VIII).

The nature of the solvent is not limiting. Exemplary solvents include, but are not limited to, ether solvents such as 1,4-dioxane, 1,2-dimethoxyethane, tetrahydrofuran (THF) and the like; alcohols such as ethanol and 2-methoxyethanol; amides such as dimethylformamide (DMF) or dimethylacetamide (DMA); aromatic solvents such as benzene, toluene or xylene; and polar solvents such as DMSO, acetic anhydride, acetic acid, tetramethylurea and the like. In some embodiments, the solvent is a mixture of acetic acid and acetic anhydride, lower fatty alcohol or a mixture of lower fatty alcohol and benzene, toluene or xylene. The lower fatty alcohol is e.g., methanol, ethanol, isopropanol and/or n-butanol. Each possibility represents a separate embodiment of the invention.

In addition, microwave conditions can reduce the reaction time to 0.5-1 h, so these conditions may be used in accordance with further embodiments of the present invention.

The substituted urea (VIII) can be prepared by standard methods of chemical synthesis known in the art, for example, in accordance with the methods described In *Science of Synthesis*, Vol. 18; Knight, J. G., Ed.; Thieme Verlag: Stuttgart, 2005, 665-758; J. *Chem. Rev.* 1996, 96, 2035; In *Ullmann's Encyclopedia of Industrial Chemistry*, 5th ed., Vol. A27; VCH: Weinheim, 1996, 355-365; In Houben-Weyl, 4th ed., Vol. E4; Hagemann, H., Ed.; Thieme Verlag: Stuttgart, 1983, 334-367; *Tetrahedron Letters*, Vol. 38, No. 9, pp. 1531-1532, 1997; *J. Org. Chem.* 2004, 69, 4741; SYNTHESIS, 2007, No. 22, pp 3497-3506; and references cited therein. The contents of each of these references are incorporated by reference as is fully set forth herein.

Alkyl- and phenyl malonate and malonic acid are commercial compounds, active esters of malonic acid can be prepared by standard methods of chemical synthesis, for example, according to well-known procedures for preparation of amino acid active esters (See: Tetrahedron 61 (2005) 10827-10852; *Current Organic Chemistry*, 2001, 5, 45-87; In: Peptide synthesis and applications/edited by John Howl. (Methods in molecular biology, v.298, 2005); In: Houben-Weyl Volume E22a-d—Synthesis of Peptides and Peptidomimetics). The contents of each of these references are incorporated by reference as is fully set forth herein.

The products of step 1, i.e., compounds (VII) or (VII-A), as well as certain compounds of formula (VIII) are novel and form further aspects of the present invention.

Step 2:

In Step 2, compound (VII) or (VII-A) is converted to a compound of formula (II) by contacting compound (VII) or (VII-A) with a reagent that introduces the group X, and/or results in the formation of group X. In one embodiment, X is a halogen (Hal), and is preferably a bromine atom or a chlorine atom, but can also be other halogens such as iodo or fluoro. In accordance with this embodiment, compound (II) can be prepared by reacting compound (VII) of (VII-A) with a halogenating agent such as phosphorous pentachloride, phosphorus oxychloride, thionyl chloride, phosphorous tribromide, N-bromosuccinimide, and the like. Preferably, the reaction is conducted in a solvent such as trifluoromethanesulfonic acid, acetic acid, concentrated sulfuric acid, N,N-dimethylformamide (DMF), and the like, or by using a halogenating agent such as phosphorus oxychloride alone, or mixtures thereof with water as a solvent, preferably at a temperature ranging from about room temperature to reflux.

In other embodiments, X is a leaving group such as a sulfonate (e.g., OMs, OTs and the like), a sulfide (e.g., SMe, SPh), imidazole (Im), benzotriazole (Bta), and the like. Each possibility represents a separate embodiment of the invention. A compound of formula (II) wherein X=OMs, OTs, SMe, SPh, imidazole (Im) or benzotriazole (Bta) can be prepared from a compound of formula (II) wherein X is Hal, or such compound can be prepared by another suitable method known to a person of skill in the art.

In one currently preferred embodiment, the reaction is performed in phosphorus oxychloride as a solvent at 60° C. to reflux. Phosphorus pentachloride can be added for acceleration of the reaction. In this case, the reaction can be performed in an organic solvent, preferably, acetonitrile, optionally in the presence of a phase transfer agent and a catalyst. When used, the catalyst is preferably a chloride anion-containing compound, more preferably, the phase transfer agent and catalyst is the same compound, such as benzyltriethylammonium chloride or alike.

In another embodiment, X is $NH_2$. In accordance with this embodiment, compound (II) can be prepared from compound (VIII) by reacting compound (VIII) with cyanoacetic acid or its ester, analogously to a known procedure (J. of Organic Chemistry (1951), 39:1879-1890), the contents of which is incorporated by reference in its entirety as if fully set forth herein. The intermediate (compound VII-A) can be converted to compound (II) upon reaction with a base, e.g., a hydroxide.

Step 3:

In Step 3, compound (II) is reacted with an amine $HNR^3R^4$ so as to displace the group X with a group $NR^3R^4$. In one embodiment, compound (I) can be obtained by reacting compound (II) (e.g., X=Hal) with compound (III) in a solvent under heating. As the solvent, alcohol solvents such as water-containing or anhydrous methanol, ethanol and the like; ether solvents such as 1,4-dioxane, tetrahydrofuran (THF) and the like, polar solvents such as DMSO, DMF, dimethylacetamide (DMA) and the like, or mixtures thereof with water and the like can be mentioned. The reaction can be carried out in the presence of a base, for example inorganic base such as sodium hydroxide, sodium hydrogen carbonate, soda ash, potassium carbonate or organic base such as a tertiary amine, including acyclic amines (for example, trimethylamine, triethylamine, dimethylphenylamine diisopropylethylamine, tributylamine), cyclic amines (for example, N-methylmorpholine) and aromatic amines (dimethylaniline, dimethylaminopyridine, pyridine). Each possibility represents a separate embodiment of the present invention.

The amine $HNR^3R^4$ is a cyclic moiety in which $R^3$ and $R^4$, together with the nitrogen to which they are attached form a 4, 5, 6 or 7 membered ring, which may be substituted. Suitable substituents include, but are not limited to, halogen, cyano, hydroxy, alkoxy, aryloxy, carbonyl, amido, alkylamido, dialkylamido, nitro, amino ($NH_2$), alkylamino, dialkylamino, carboxyl, thio and thioalkyl.

In one embodiment, compound (III) is a diamine of formula (V): $HNR^6R^7NHR^8$, wherein $R^8$ is H or a nitrogen protecting group as described herein or as is otherwise known to a person of skill in the art. $R^6$ and $R^7$ together with the nitrogen to which they are attached form a 4, 5, 6 or 7 membered ring, $NHR^8$ is a substituent at any position of such ring, and $R^8$ is H or a nitrogen protecting group. In one currently preferred embodiment, $HNR^3R^4$ is represented by the structure:

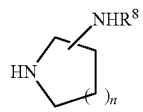

wherein $R^8$ is H or a nitrogen protecting group, and n is 0, 1 or 2.

In one embodiment, $HNR^3R^4$ is represented by the structure

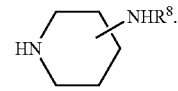

In another embodiment, $HNR^3R^4$ is represented by the structure

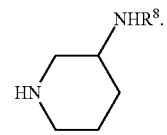

In yet another embodiment, $R^3$ and $R^4$ together with the nitrogen to which they are attached form a ring represented by the structure:

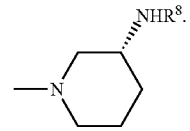

Each possibility represents a separate embodiment of the invention.

In another embodiment, compound of formula (III) or (V) is a cyclic diamine, N-protected by an acid labile protecting group. In one embodiment, the compound of formula (III) or (V) is (R)-piperidin-3-yl-carbamic acid tert-butyl ester.

In one embodiment, compound (I) can be obtained by reacting compound (II) (X=OH) with compound (III) under Mitsunobu type coupling conditions (in the presence of a coupling reagent and an activating agent) in an organic solvent, such as THF while stirring for about 5-10 h at a temperature ranging from room temperature to 40-50° C.

In another embodiment, compound (I) can be obtained by reacting compound (II) (X=SMe) with compound (III) in an organic solvent such as toluene at a temperature ranging from 80° C. to reflux.

In yet another embodiment, compound (I) can be obtained by reacting compound (II) (X=$NH_2$) with compound (III) as a free base or in the form of salts with inorganic or organic acid, preferably, in the form of a hydrochloride salt.

Step 4:

In accordance with optional step 4, compound (IV) can be prepared by reacting compound (I) with an acid HY in a solvent at room temperature or under heating.

Optionally, step 3 and step 4 can be combined into a single step without separation and purification of compound (I). In accordance with this embodiment, compound (II) is reacted with amine (III) followed by a reaction with an acid HY, in one step without isolation of any intermediates. For example, for the embodiment wherein amine (III) is represented by the structure of compound (V), the steps of reacting compound (II) with a compound (V) to generate compound (VI) followed by reaction with an acid HY can be conducted in one stage without separation or purification of any intermediates. In accordance with this embodiment, the process of the invention comprises the steps of: (a) reacting a compound of formula (II) with a diamine of formula (V) under conditions sufficient to form compound (VI); (b) reacting compound (VI) with acid HY to form a salt as one-stage synthesis without separation and purification of compound (VI); and (c) optionally, if needed, removing the protecting group so as to form a compound of formula (I).

Y is a counter-ion selected from the group consisting of acetate, trifluoroacetate, citrate, hydrochloride, L-lactate, succinate, benzoate and L-tartrate. The corresponding acid HY is acetic acid, trifluoroacetic acid, citric acid, hydrochloric acid, L-lactic acid, succinic acid, benzoic acid or L-tartaric acid. A currently preferred acid is benzoic acid.

Some examples of the production methods of the compounds encompassed by the present invention are shown in the following section. However, the production methods of the compounds of the present invention are not limited to these examples. Modifications and alternative embodiments can be afforded as known to a person of skill in the art by designs such as introducing, where necessary, a protecting group into a functional group followed by deprotection in a subsequent step; subjecting a functional group to each step as a precursor and converting the group to a desired functional group in a suitable step; exchanging the order of respective production methods and steps; and the like.

The work-up treatment in each step can be applied by a typical method, wherein isolation and purification is performed as necessary by selecting or combining conventional methods, such as crystallization, recrystallization, distillation, partitioning, silica gel chromatography, preparative HPLC and the like.

CHEMICAL DEFINITIONS

An "alkyl" group as used herein refers to any saturated aliphatic hydrocarbon, including straight-chain, branched-chain and cyclic alkyl groups (cycloalkyl). In one embodiment, the alkyl group has 1-10 carbons designated here as $C_1$-$C_{10}$-alkyl. In another embodiment, the alkyl group has 1-6 carbons designated here as $C_1$-$C_6$-alkyl. In another embodiment, the alkyl group has 1-4 carbons designated here as $C_1$-$C_4$-alkyl. The alkyl group may be unsubstituted or substituted by one or more groups including, but not limited to from halogen, cyano, hydroxy, alkoxy, aryloxy, carbonyl, amido, alkylamido, dialkylamido, nitro, amino ($NH_2$), alkylamino, dialkylamino, carboxyl, thio and thioalkyl.

A "cycloalkyl" group refers to a non-aromatic mono- or multicyclic ring system. In one embodiment, the cycloalkyl group has 3-10 carbon atoms. In another embodiment, the cycloalkyl group has 5-10 carbon atoms. Exemplary monocyclic cycloalkyl groups include cyclopentyl, cyclohexyl, cycloheptyl and the like. An alkylcycloalkyl is an alkyl group as defined herein bonded to a cycloalkyl group as defined herein. The cycloalkyl group can be unsubstituted or substituted with any one or more of the substituents defined above for alkyl.

An "Ar" group, i.e., an aryl group, refers to an aromatic ring system containing from 6-14 ring carbon atoms. The aryl ring can be a monocyclic, bicyclic, tricyclic and the like. Non-limiting examples of aryl groups are phenyl, naphthyl including 1-naphthyl and 2-naphthyl, and the like. A currently preferred Ar group is phenyl. An alkylaryl refers to an alkylene group (e.g., $CH_2$) which is substituted by an aryl group. The aryl group can be unsubstituted or substituted through available carbon atoms with one or more groups defined hereinabove for alkyl.

All stereoisomers of the above compounds are contemplated, either in admixture or in pure or substantially pure form. The compounds of the present invention can have asymmetric centers at any of the atoms. Consequently, the compounds can exist in enantiomeric or diastereomeric forms or in mixtures thereof. The present invention contemplates the use of any racemates (i.e. mixtures containing equal amounts of each enantiomers), enantiomerically enriched mixtures (i.e., mixtures enriched for one enantiomer), pure enantiomers or diastereomers, or any mixtures thereof. The chiral centers can be designated as R or S or R,S or d,D, l,L or d,l, D,L.

As used herein, unless otherwise noted, the term "nitrogen protecting group" refers to a group which may be attached to a nitrogen atom to protect said nitrogen atom from participating in a reaction and which may be readily removed following the reaction. The nitrogen protecting group can be an acid labile protecting group, a base labile protecting group, or a protecting group that is removable under neutral conditions. Common N-protecting groups comprise acyl groups such as acetyl, benzoyl, 2-bromoacetyl, 4-bromobenzoyl, tert-butylacetyl, carboxaldehyde, 2-chloroacetyl, 4-chlorobenzoyl, a-chlorobutyryl, 4-nitrobenzoyl, o-nitrophenoxyacetyl, phthalyl, pivaloyl, propionyl, trichloroacetyl, and trifluoroacetyl; sulfonyl groups such as benzenesulfonyl, and p-toluenesulfonyl; carbamate groups of the formula —C(O)O—R wherein R is for example methyl, ethyl, t-butyl, benzyl, phenylethyl, $CH_2$=CH—$CH_2$, such as benzyloxycarbonyl (Cbz), tert-butyloxycarbonyl (Boc), p-chlorobenzyloxycarbonyl, p-methoxybenzyloxycarbonyl, and the like. A currently preferred nitrogen protecting groups is tert-Butyloxycarbonyl (Boc). Other suitable nitrogen protecting group include, but are not limited to: (Fmoc), p-nitrobenzenesulfoethoxycarbonyl propargyloxycarbonyl, picolinyl, prenyl, o-nitrobenzyloxy methyl, 4-methyoxyphenoxymethyl, guaiacolmethyl, siloxymethyl, such as triisopropylsiloxymethyl, 2-cyanoethyoxymethyl, 2-quinolinylmethyl, dichloroacetyl, trichloroacetyl and 2-[4-nitrophenyl]ethylsulfonate, as well as benzyl, p-methoxy benzyl, trityl, cbz groups which are all readily cleaved via hydrogenation. Each possibility represents a separate embodiment of the invention.

Other examples of nitrogen-protecting groups are described by C. B. Reese and E. Haslam, "Protective Groups in Organic Chemistry," J. G. W. McOmie, Ed., Plenum Press, New York, N.Y., 1973, Chapters 3 and 4, respectively, and T. W. Greene and P. G. M. Wuts, "Protective Groups in Organic Synthesis," $2^{nd}$ ed., John Wiley and Sons, New York, N.Y., 1991, Chapters 2 and 3, each of which is incorporated herein by reference.

EXPERIMENTAL DETAILS SECTION

Specific compounds which are representative of this invention were prepared as per the following examples and reaction sequences; the examples and the diagrams depicting the reaction sequences are offered by way of illustration, to aid in the understanding of the invention and should not be construed to limit in any way the invention set forth in the claims which follow thereafter. The instant compounds may also be used as intermediates in subsequent examples to produce additional compounds of the present invention. One skilled in the art would know how to vary yields through routine variations in reaction times, temperatures, solvents and/or reagents.

Unless otherwise noted, the materials used in the examples were obtained from readily available commercial suppliers or synthesized by standard methods known to one skilled in the art of chemical synthesis. The substituent groups, which vary between examples, are hydrogen unless otherwise noted.

Example 1

Preparation of (R)-2-((6-(3-aminopiperidin-1-yl)-3-methyl-2,4-dioxo-3,4-dihydropyrimidin-1 (2H)-yl) methyl)benzonitrile (alogliptin) via 6-chloro-1-(2-isocyanobenzyl)-3-methylpyrimidine-2,4(1H,3H)-dione (Scheme 3)

Water (1 L) was added and stirred for 30 min. The obtained solid was collected by filtration and dried in oven at 50° C. for 12 h. The yield is 85% and the purity 99.8%.

Preparation of 1-(2-isocyanobenzyl)-3-methylpyrimidine-2,4,6(1H,3H,5H)-trione a). To a stirred solution of 0.11 mol of sodium ethanolate in 80 ml of ethanol abs. was added 0.1 mol of 1-(2-isocyanobenzyl)-3-methylurea and 0.1 mol diethyl malonate. The mixture was refluxed for 3-5 h. The cooled residue was acidified with 0.1 M hydrochloric acid (60 ml). The solid which separated was filtered off and recrystallized from ethanol or any suitable solvent. The yield is 78-85% and purity >95%.

b). In an alternate embodiment, 1-(2-isocyanobenzyl)-3-methylurea (30 g), acetic acid (105 ml) and malonic acid (18 g) were mixed and heated to 60° C. Acetic anhydride (60 ml) was added at 60° C. and heating was continued for two hours

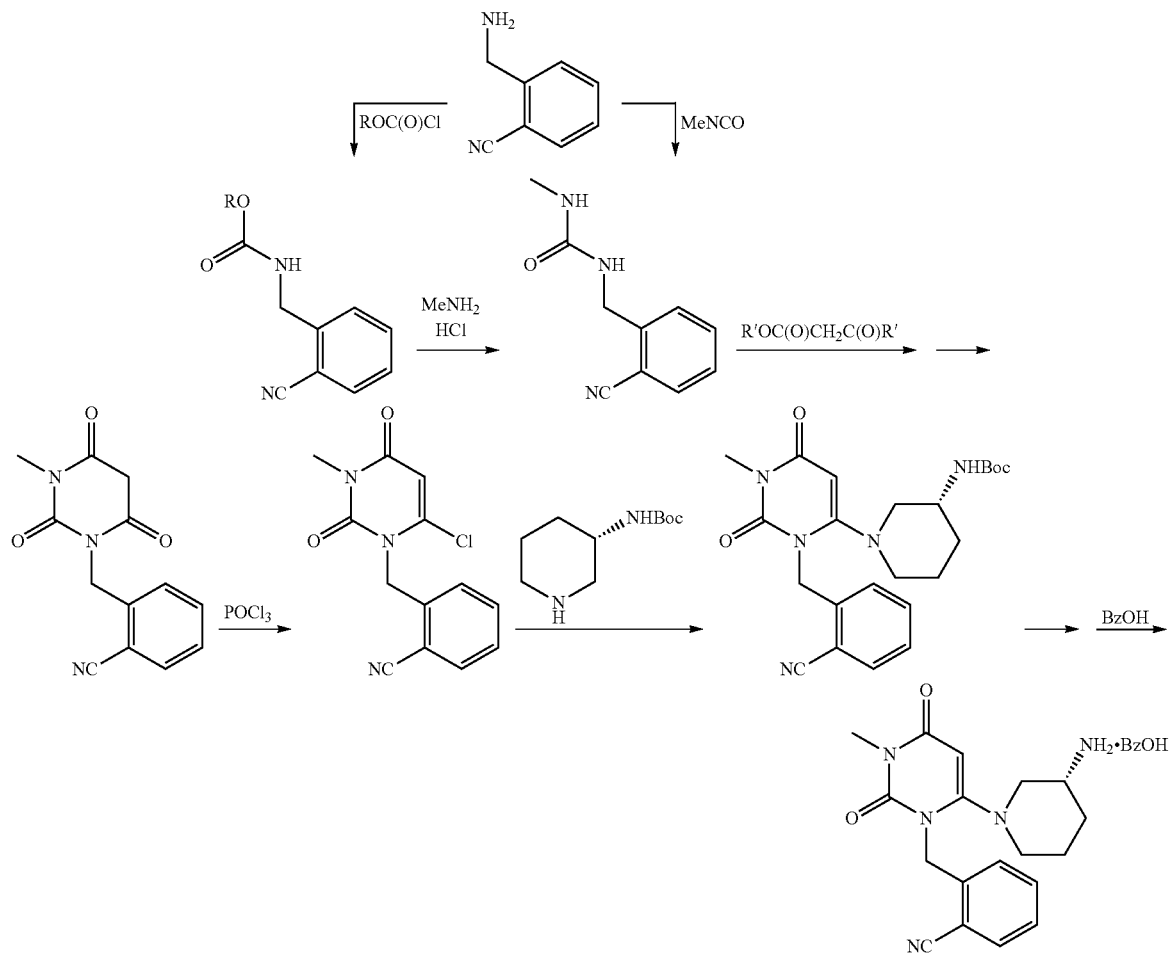

Scheme 3

Preparation of 1-(2-isocyanobenzyl)-3-methylurea 2-cyanobenzylamine hydrochloride (90 g) and Dichloromethane (800 ml) were taken into a round bottomed (RB) flask. Methyl isocyanate (45.6 g) was added at 5° C. Triethylamine (81 g) in Dichloromethane (300 ml) was added at the same temperature and stirred at room temperature for 16 h.

at 80° C. The reaction mixture was poured over ice water (300 ml) and the obtained solid was filtered, washed with water (1×500 ml) and methyl-tert-butylether (100 ml). The yield is 60% with 93.4% purity.

The compound thus prepared can be used for the next step without purification or purified by crystallization or column chromatography.

Preparation of 6-chloro-1-(2-isocyanobenzyl)-3-methylpyrimidine-2,4(1H,3H)-dione a). 1-(2-isocyanobenzyl)-3-methylpyrimidine-2,4,6(1H,3H,5H)-trione (30 g) was mixed with phosphorus oxychloride (300 ml) and cooled to 0° C. Water (9 ml) was added slowly, stirred for 10 min. and heated to reflux at 110° C. for 5 h. Progress of the reaction was monitored by TLC (50% Ethyl acetate/Hexane). On completion of the reaction, phosphorus oxychloride was distilled off. The crude compound was dissolved in dichloromethane (500 ml) and poured into ice water (500 ml) by small portions. The layers were separated and the aqueous layer was extracted with dichloromethane (200 ml). The combined organic extracts were washed with water and brine, dried over sodium sulphate and concentrated under reduced pressure. The mixture of two isomers (4-chloro and 6-chloro derivatives=1:1) was isolated and separated by column chromatography using neutral alumina and eluent—25-50% of ethylacetate and hexane). The off-white solid was obtained, yield—37%, purity—99.8%. $^1$H NMR corresponds to literature data (*J. Med. Chem.* 2007, 50, 2297-2300).

b). In an alternate embodiment, a solution of 1-(2-isocyanobenzyl)-3-methylpyrimidine-2,4,6(1H,3H,5H)-trione (18 mmol), phosphorus oxychloride (85 ml), benzyltriethylammonium chloride (16.5 g, 72 mmol) and phosphorus pentachloride (3.8 g, 18 mol) in acetonitrile (80 ml) was refluxed for 4-5 h with stirring. After evaporation under reduced pressure, the resulting oily residue was mixed with methylene chloride (or chloroform) and the mixture was poured into water and ice (50 ml). The layers were separated and the aqueous layer was extracted with dichloromethane (200 ml). The combined organic extracts were washed with water and brine, dried over sodium sulphate and concentrated under reduced pressure. Crude product was crystallized from THF-hexanes to give desired compound in 70.5% yield.

c). In an alternate embodiment, a solution of 1-(2-isocyanobenzyl)-3-methylpyrimidine-2,4,6(1H,3H,5H)-trione (13.1 mmol) in POCl$_3$ (30 ml) was refluxed for 1-3 h. The solvent was concentrated and then partitioned with CH$_2$Cl$_2$ (100 ml) and water (100 ml). The organic layer was washed with brine, dried over Na$_2$SO$_4$, and concentrated to give 6-chloro compound as a solid (~95%). Compound can be also precipitated from concentrated methylene chloride solution by hexanes and used as a crude for the next step or purified by reslurring in isopropanol, filtered off, washed with isopropanol, and dried under vacuum at 55-60° C.

Preparation of (R)-tert-butyl 1-(3-(2-isocyanobenzyl)-1-methyl-2,6-dioxo-1,2,3,6-tetrahydropyrimidin-4-yl)piperidin-3-yl carbamate a). 6-chloro-1-(2-isocyanobenzyl)-3-methylpyrimidine-2,4(1H,3H)-dione (13 g), Dimethylformamide (130 ml), Potassium carbonate (13 g) and tert-butyl (R)-piperidin-3-ylcarbamate (10.4 g) were heated to 80° C. for 7 hrs. The mixture was then allowed to come to room temperature and poured over ice water (500 ml). The obtained solid was filtered and washed with cold water (500 ml). The solid thus obtained was taken in Methyl-tert-butylether (50 ml) stirred for 10 min. filtered and washed with Hexane (50 ml), to give the N-tert-butyloxycarbonyl protected compound in ~75% yield.

b). In an alternate embodiment, a flask charged with a stir bar, 6-chloro-1-(2-isocyanobenzyl)-3-methylpyrimidine-2,4(1H,3H)-dione (4.10 mmol), (R)-3-tertbutyloxycarbonylaminopiperidine (4.64 mmol), K$_2$CO$_3$ (1.15 g, 8.32 mmol) and DMF (12 mL) was stirred at 75° C. for 6 h. Then, water was added and the mixture was extracted with methylene chloride. The organic layer was washed with brine, dried over Na$_2$SO$_4$, and concentrated to give the N-tertbutyloxycarbonyl protected compound in ~93-96% yield.

Preparation of (R)-2-((6-(3-aminopiperidin-1-yl)-3-methyl-2,4-dioxo-3,4-dihydropyrimidin-1(2H)-yl)methyl)benzonitrile salts a). Preparation of (R)-2-(6-(3-aminopiperidin-1-yl)-3-methyl-2,4-dioxo-3,4-dihydropyrimidin-1(2H)-yl)methyl)benzonitrile hydrochloride The crude (R)-tert-butyl 1-(3-(2-isocyanobenzyl)-1-methyl-2,6-dioxo-1,2,3,6-tetrahydropyrimidin-4-yl)piperidin-3-yl carbamate from previous procedure was dissolved in THF and acidified with 6M hydrochloric acid while maintaining the temperature below 15° C. The resultant slurry was cooled to 0-5° C., stirred at this temperature for 3-5 h and then filtered. The filter cake was washed twice with isopropanol and dried in vacuum at 45-50° C. to provide hydrochloride as a white crystalline solid.

b). Preparation of (R)-2-(6-(3-aminopiperidin-1-yl)-3-methyl-2,4-dioxo-3,4-dihydropyrimidin-1(2H)-yl)methyl)benzonitrile trifluoroacetate TFA (1 mL) was added into the methylene chloride solution of (R)-tert-butyl 1-(3-(2-isocyanobenzyl)-1-methyl-2,6-dioxo-1,2,3,6-tetrahydropyrimidin-4-yl)piperidin-3-yl carbamate from the above-mentioned procedure. The solution was stirred at room temperature for 1 h and then the mixture was concentrated in vacuo. The residue was dissolved in a small amount of MeOH or isopropanol and the desired salt was precipitated by addition of diisopropyl ether. The solids were filtered off, washed with diisopropyl ether and dried in vacuum at 45-50° C. to provide trifluoroacetate as an off-white powder.

c). Preparation of (R)-2-((6-(3-aminopiperidin-1-yl)-3-methyl-2,4-dioxo-3,4-dihydropyrimidin-1(2H)-yl)methyl)benzonitrile benzoate (Alogliptin)

The crude (R)-tert-butyl 1-(3-(2-isocyanobenzyl)-1-methyl-2,6-dioxo-1,2,3,6-tetrahydropyrimidin-4-yl)piperidin-3-yl carbamate was dissolved in ethanol. A solution of benzoic acid in ethanol was added and the mixture was slowly heated to 65-70° C. The solution was stirred at this temperature for 1 h and was then crystallized by cooling to 0-5° C. and stirring for 12 hrs. The solution was filtered, washed with alcohol. The wet cake was then conditioned under nitrogen for 2 hours. The cake was dried for 8 hrs at 40-50° C. to provide the benzoic acid salt of alogliptin as a white crystalline solid.

Example 2

Preparation of (R)-2-((6-(3-aminopiperidin-1-yl)-3-methyl-2,4-dioxo-3,4-dihydropyrimidin-1(2H)-yl)methyl)benzonitrile (alogliptin) via 6-amino-1-(2-isocyanobenzyl)-3-methylpyrimidine-2,4(1H,3H)-dione (Scheme 4)

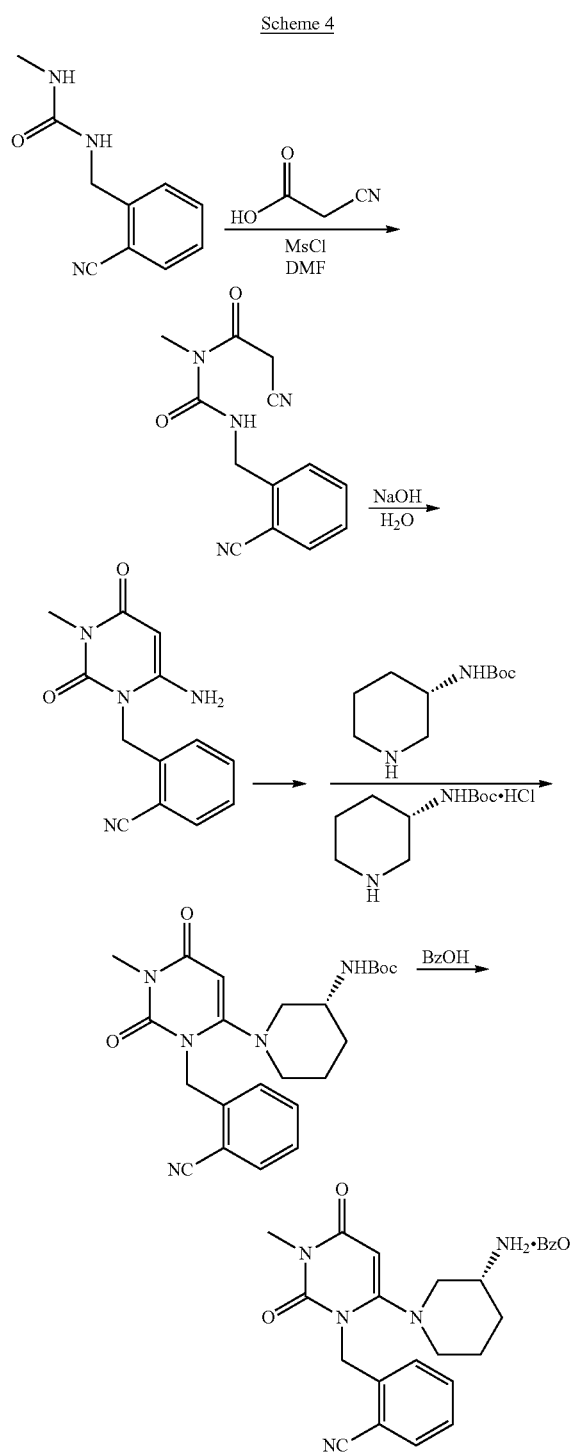

Scheme 4

Preparation of 6-amino-1-(2-isocyanobenzyl)-3-methylpyrimidine-2,4(1H,3H)-dione a). 1-(2-isocyanobenzyl)-3-methylurea (0.2 mol) and cyanoacetic acid (0.22 mol) were dissolved in acetic anhydride (400 ml), and the mixture was heated at 80° C. for 2 hours. Acetic anhydride was distilled off under reduced pressure and water (200 ml) was added. The mixture was cooled to 0-5° C. and 2N NaOH solution (220 ml) was added and stirring was continued for 2 hours. The obtained solids were filtered off, washed with cold methanol and dried under vacuum. The yield of 6-amino-1-(2-isocyanobenzyl)-3-methylpyrimidine-2,4(1H,3H)-dione was 72%.

b). Under nitrogen atmosphere, 1-(2-isocyanobenzyl)-3-methylurea (98.4 g) and cyanoacetic acid (80.0 g) was added to N,N-dimethylformamide (836 ml). The mixture was stirred at room temperature and methanesulfonyl chloride (72.8 ml) was added dropwise with stirring at this temperature. The mixture was stirred at room temperature for 4 hrs, cooled with water, and water-isopropanol [2:1 (volume ratio), 1670 ml] was added drop wise. The mixture was stirred under water-cooling for 1 hr, and the precipitated crystals were collected by filtration and dried to give 3-(2-cyano-acetyl)-3-methyl-1-(2-isocyanobenzyl)-urea with 68% yield.

To 3-(2-cyano-acetyl)-3-methyl-1-(2-isocyanobenzyl)-urea (120 g) were added water (962 ml) and 2N aqueous sodium hydroxide solution (24.9 ml), and the mixture was stirred with heating at 80° C. for 1 hr. After allowing to cool to room temperature, the crystals were collected by filtration and dried to give 6-amino-1-(2-isocyanobenzyl)-3-methylpyrimidine-2,4(1H,3H)-dione in 76% yield.

c). 6-amino-1-(2-isocyanobenzyl)-3-methylpyrimidine-2,4(1H,3H)-dione (0.1 mol) was mixed with (R)-piperidin-3-yl-carbamic acid tert.-butyl ester hydrochloride (0.1 mol) of the appropriate amine hydrochloride and (R)-piperidin-3-yl-carbamic acid tert.-butyl ester (0.1 mol). The mixture was heated at 100° C. and bubbling continued for 3 hr. Water was added to the cooled mixture and the mixture was extracted with methylene chloride. The organic layer was washed with brine, dried over $Na_2SO_4$, and concentrated to give N-tert-butyloxycarbonyl protected compound in ~93-96% yield.

d). Benzoate salt of alogliptin was prepared as described above.

While certain embodiments of the invention have been illustrated and described, it will be clear that the invention is not limited to the embodiments described herein. Numerous modifications, changes, variations, substitutions and equivalents will be apparent to those skilled in the art without departing from the spirit and scope of the present invention as described by the claims, which follow.

The invention claimed is:
1. A process for producing a pyrimidin-dione derivative represented by the structure of formula (I):

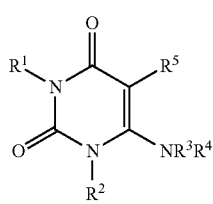

(I)

wherein:

$R^1$ and $R^5$ are each independently H or $(C_1\text{-}C_{10})$alkyl, $R^2$ is $CH_2Ar$, and $R^3$ and $R^4$ together with the nitrogen to which they are attached form a 4, 5, 6 or 7 membered ring, which may be unsubstituted or substituted;

the process comprising the steps of:

1) reacting a urea derivative of Formula (VIII):

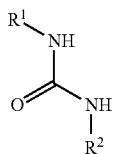
(VIII)

with malonic acid or its derivatives of formulae $RO_2CCH(R^5)CO_2R$ or $RO_2CCH(R^5)CN$, so as to form a compound of formula (VII) or (VII-A):

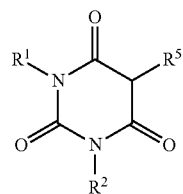
(VII)

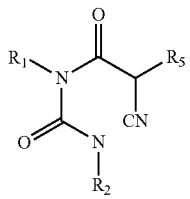
(VII-A)

wherein R is H, $(C_1\text{-}C_{10})$alkyl, phenyl or N-oxysuccinimidyl ester, wherein each of the alkyl or phenyl may be unsubstituted or substituted;

2) reacting compounds (VII) or (VII-A) with a reagent that introduces or forms the group X, so as to form a compound of the formula (II):

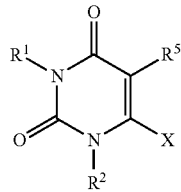
(II)

wherein X is a leaving group; and 3) reacting compound (II) with a reagent of Formula (III): $HNR^3R^4$ so as to form the compound of Formula (I)

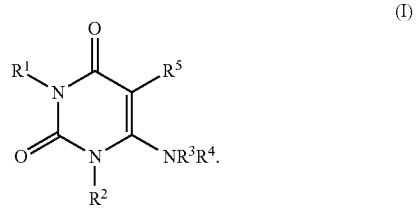
(I)

2. The process of claim 1, wherein X is selected from the group consisting of halogen, OTs, OMs, SMe, SPh, Im, Bta, and $NH_2$.

3. The process of claim 1, further comprising the step of converting the pyrimidin-dione product of formula (I) to a salt of formula (IV) by reacting the compound of formula (I) with an acid HY

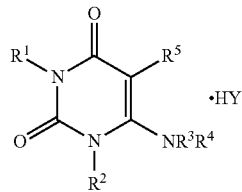
(IV)

wherein Y is a counter-ion selected from the group consisting of acetate, trifluoroacetate, citrate, hydrochloride, L-lactate, succinate, benzoate and L-tartrate.

4. The process of claim 1, wherein $HNR^3R^4$ of formula (III) is a diamine of formula (V): $HNR^6R^7\text{---}NHR^8$, wherein $R^6$ and $R^7$ together with the nitrogen to which they are attached form a 4, 5, 6 or 7 membered ring, $NHR^8$ is a substituent of such ring, and $R^8$ is H or a nitrogen protecting group.

5. The process of claim 4, wherein $HNR^6R^7\text{---}NHR^8$ is represented by the structure:

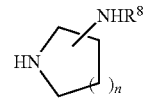

wherein $R^8$ is H or a nitrogen protecting group, and n is 0, 1 or 2.

6. The process of claim 1, wherein step (3) comprises reacting a compound of formula (II) with a diamine of formula (V): $HNR^6R^7\text{---}NHR^8$, so as to form a compound of formula (VI)

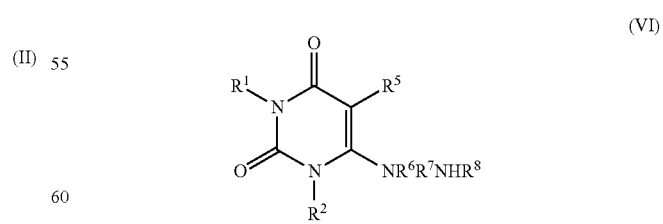
(VI)

wherein $R^1$, $R^2$ and $R^5$ are as defined in claim 1;

$R^6$ and $R^7$ together with the nitrogen to which they are attached form a 4, 5, 6 or 7 membered ring, $NHR^8$ is a substituent of such ring; and $R^8$ is a nitrogen protecting group.

7. The process of claim 6, wherein the compound of formula (VI) is represented by the structure of formula (VI-A) or (VI-B):

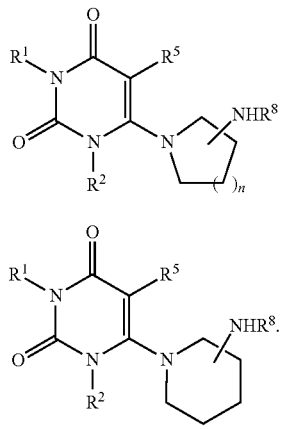

8. The process of claim 6, comprising the steps of
(a) reacting a compound of formula (II) with a diamine of formula (V) so as to form compound (VI);
(b) reacting compound (VI) with acid HY to form a salt as one-stage synthesis without separation and purification of compound (VI); and
(c) optionally, removing the protecting group so as to form a compound of formula (I).

9. The process of claim 8, wherein the protecting group is removed in step (b) upon treatment with acid HY, and step (c) is not performed.

10. The process of claim 1, wherein $R^1$ is methyl.

11. The process of claim 1, wherein $R^2$ is —(CH$_2$)-(2-cyanophenyl).

12. The process of claim 1, wherein
$R^3$ and $R^4$ together with the nitrogen to which they are attached form a ring represented by the structure:

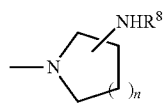

wherein $R^8$ is H or a nitrogen protecting group, and n is 0, 1 or 2; or $R^3$ and $R^4$ together with the nitrogen to which they are attached form a ring represented by the structure:

13. The process of claim 1, wherein the compound of formula (III) is (R)-piperidin-3-yl-carbamic acid tert-butyl ester.

14. The process of claim 1, wherein $R^5$ is H.

15. The process of claim 1, wherein the pyrimidin-dione of the formula (I) is 2-[6-[3(R)-Aminopiperidin-1-yl]-3-methyl-2,4-dioxo-1,2,3,4-tetrahydropyrimidin-1-ylmethyl] benzonitrile (alogliptin), or a salt thereof.

16. The process of claim 15, wherein the salt is a benzoate salt (alogliptin benzoate).

17. The process of claim 1, wherein X is halogen and step (2) comprises reacting a compound of formula (VII)

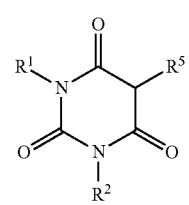

with a halogen containing reagent selected from the group consisting of phosphorous oxychloride, phosphorous pentachloride, thionyl chloride, phosphorous tribromide, and N-bromosuccinimide, so as to introduce or form the group X.

18. The process of claim 1, wherein the malonic acid derivative is a malonic acid ester selected from the group consisting of methyl, ethyl, unsubstituted or substituted phenyl or N-oxysuccinimidyl ester.

* * * * *